United States Patent
Niklaus

(10) Patent No.: US 10,980,937 B2
(45) Date of Patent: Apr. 20, 2021

(54) DOSING UNIT FOR USE IN AMBULATORY INFUSION SYSTEMS

(71) Applicant: Roche Diabetes Care, Inc., Indianapolis, IN (US)

(72) Inventor: Hanspeter Niklaus, Riken (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 197 days.

(21) Appl. No.: 15/908,076

(22) Filed: Feb. 28, 2018

(65) Prior Publication Data

US 2018/0185570 A1    Jul. 5, 2018

Related U.S. Application Data

(63) Continuation of application No. PCT/EP2016/070200, filed on Aug. 26, 2016.

(30) Foreign Application Priority Data

Sep. 3, 2015   (EP) ..................... 15183667

(51) Int. Cl.
*A61M 5/14* (2006.01)
*A61M 5/142* (2006.01)
*A61M 5/315* (2006.01)
*F04B 53/14* (2006.01)
(Continued)

(52) U.S. Cl.
CPC .... *A61M 5/14216* (2013.01); *A61M 5/31513* (2013.01); *F04B 13/00* (2013.01);
(Continued)

(58) Field of Classification Search
CPC .......... A61M 5/31501; A61M 5/31513; A61M 2025/3101
See application file for complete search history.

(56) References Cited

U.S. PATENT DOCUMENTS 5,314,416 A  *  5/1994  Lewis ............... A61M 5/31513
                                                          600/576
2008/0300551 A1   12/2008  Schiller et al.
(Continued)

FOREIGN PATENT DOCUMENTS

EP   1970677 A1   9/2008
EP   2163273 A1   3/2010
(Continued)

OTHER PUBLICATIONS

International Search Report and Written Opinion of the International Searching Authority; PCT/EP2016/070200; dated Dec. 16, 2016; 13 pages.

*Primary Examiner* — Nathan R Price
*Assistant Examiner* — Tania Ismail
(74) *Attorney, Agent, or Firm* — Bose McKinney & Evans LLP

(57) ABSTRACT

A dosing unit for use in an ambulatory infusion system, the dosing unit including: a dosing cylinder and a piston arranged inside the dosing cylinder and in a sliding displaceable manner along a displacement axis. The piston is convertible from a storing configuration into an operational configuration, wherein a circumferential sealing member of the piston is mechanically relieved in the storing configuration and is in sealing and sliding engagement with a circumferential inner surface of the dosing cylinder in the operational configuration. The dosing unit includes a configuration switch member in operative mechanical coupling with the piston, the configuration switch member being movable relative to the piston from a storing position into an operational position, thereby switching the piston configuration from the storing configuration to the operational configuration.

21 Claims, 2 Drawing Sheets

(51) Int. Cl.
  *F04B 13/00* (2006.01)
  *A61M 5/145* (2006.01)
  *A61M 5/168* (2006.01)
  *F04B 53/16* (2006.01)
(52) U.S. Cl.
  CPC ........... *F04B 53/14* (2013.01); *A61M 5/1452* (2013.01); *A61M 5/16804* (2013.01); *A61M 5/31515* (2013.01); *F04B 53/16* (2013.01)

(56) References Cited

U.S. PATENT DOCUMENTS

2010/0256486 A1* 10/2010 Savage ................. A61M 5/007
  600/432
2014/0180210 A1* 6/2014 Niklaus ............. A61M 5/14216
  604/152

FOREIGN PATENT DOCUMENTS

| | | |
|---|---|---|
| EP | 2361646 A1 | 8/2011 |
| EP | 2457602 A1 | 5/2012 |
| EP | 2510960 A1 | 10/2012 |
| EP | 2510962 A1 | 10/2012 |
| EP | 2696915 B1 | 5/2017 |
| EP | 2750735 B1 | 9/2017 |
| FR | 1500009 A | 11/1967 |
| WO | WO 00/25844 | 5/2000 |
| WO | WO 02/04049 A1 | 1/2002 |
| WO | WO 2012/069308 A1 | 5/2012 |
| WO | WO 2013/010561 A1 | 1/2013 |
| WO | WO 2013/029999 A1 | 3/2013 |
| WO | WO 2013/034159 A1 | 3/2013 |
| WO | WO 2013/045592 A2 | 4/2013 |

* cited by examiner

DOSING UNIT FOR USE IN AMBULATORY INFUSION SYSTEMS

RELATED APPLICATIONS

This application is a continuation of PCT/EP2016/070200, filed Aug. 26, 2016, which claims priority to EP 15183667.3, filed Sep. 3, 2015, the entire disclosures of which are hereby incorporated herein by reference.

The present disclosure lies in the field of dosing units for an ambulatory infusion system. This disclosure lies further in the field of ambulatory infusion systems that include a dosing unit. Furthermore, this disclosure lies in the field of methods initializing a dosing unit.

Ambulatory infusion devices are well known in the art for example in the therapy of Diabetes Mellitus by Continuous Subcutaneous Insulin Infusion (CSII) as well as in pain therapy or cancer therapy and are available from a number of suppliers, such as Roche Diagnostics GmbH, Germany, or Medtronic MiniMed Inc., CA, USA.

EP 1970677 A1 discloses a system with a miniaturized metering piston pump with a dosing cylinder that is repeatedly coupled to and filled from a larger reservoir, followed by coupling the dosing cylinder to an infusion site and infusing the liquid drug out of the dosing cylinder in incremental steps and over an extended time period via displacing a piston. For alternatively coupling the dosing cylinder to the reservoir and the infusion site, a valve system is proposed. Reference is made to the EP 1970677 A1 for the basic operational principle and design of a dosing unit in accordance with the present document.

To ensure safe operation, the piston must be in sliding and sealing engagement with the inner wall of a metering cavity (bore) of the dosing cylinder. In order to achieve a sealing engagement and accordingly liquid tightness, a sealing member of the piston needs to be biased against the inner wall of the metering cavity. At least the sealing member of the piston is made from a comparably soft material, such as an elastomer or thermoplastic elastomer.

While the dosing unit is typically designed as disposable and its actual application time (i.e., the time in which it is used for drug infusion) lies in a typical range of some days, the dosing unit may be stored for a time period of up to one year or even more prior to being actually used. (Thermoplastic) elastomers, however, are known to significantly creep if tensioned or biased over an extended time period. Creep of the piston in the sealing member results in a reduced fluidic tightness or even complete loss of fluidic tightness. Maintaining fluidic tightness over the storing time and application time is accordingly a crucial and critical issue.

SUMMARY

This disclosure teaches an improvement regarding fluidic tightness of a dosing unit.

This disclosure is based on the insight that fluidic tightness, while being essential during application of the dosing unit for drug infusion, is not required for the preceding storing period. For the storing period, the dosing unit may accordingly be in a configuration where it is relieved, i.e., unbiased or biased only to an extent where creep may be ignored. In this configuration, however, the engagement between piston and dosing cylinder may not be tight.

According to an aspect, a dosing unit is provided for use in an ambulatory infusion system. A dosing unit in accordance with the present disclosure includes a dosing cylinder and a piston. The piston is arranged inside the dosing cylinder. The piston is arranged in a sliding displaceable manner along a displacement axis.

The inner volume of the dosing cylinder in which the piston is arranged is also referred to as "metering cavity." The metering cavity typically has a cylindrical or sectionwise cylindrical shape and extends along the displacement axis.

The piston is convertible from a storing configuration into an operational configuration. A circumferential sealing member of the piston is mechanically relieved in the storing configuration and is in sealing and sliding engagement with a circumferential inner surface of the dosing cylinder in the operational configuration.

The dosing unit further includes a configuration switch member. The configuration switch member is typically in operative mechanical coupling with the piston. The configuration switch member is movable relative to the piston from a storing position into an operational position, thereby switching the piston configuration from the storing configuration to the operational configuration.

A force may be exerted onto the circumferential sealing member by the configuration switch member directly or via the piston as intermediate component. For this purpose, the piston may be radially elastic.

Storing the piston and in particular its circumferential sealing member in the relieved storing configuration has the before-discussed advantage that the circumferential sealing member does not creep over time. Accordingly, the time period for which the dosing unit may be stored prior to its use without adversely affecting its characteristics and specifications is increased.

Favorably, the switching from the storing configuration to the operational configuration is irreversible. In this way, it is ensured that the operational configuration is maintained over the application time of the dosing unit.

In some embodiments, the dosing unit includes a valve unit that is reversibly switchable between a filling configuration and a draining configuration, wherein the valve unit fluidically couples the dosing cylinder with a filling port in the filling configuration and with a draining port in the draining configuration.

In such embodiments that include a valve unit, the dosing unit may especially be designed in accordance with the disclosure of the EP 1970677 A1 as discussed before.

This disclosure, however, may equally be applied to dosing units and ambulatory infusion systems of different general designs. The dosing cylinder may include a typically cylindrical drug cartridge, such as an insulin cartridge, that comprises a liquid volume in a range of, e.g., 1 ml to 4 ml, sufficient for uninterrupted infusion therapy for a number of days or even a week or more. Similar to the use of the cylinder of a dosing unit in accordance with the EP 1970677 A1, the liquid is administered from the cartridge substantially continuously and in incremental steps. Such cartridge, however, is not refilled from a larger reservoir but is discarded after emptying. In such embodiments, a valve unit is not required. Corresponding infusion pumps are also referred to as syringe-driver pumps.

In this document, the following terminology is used: The terms "proximal" and "distal" indicate directions along the displacement axis. A piston movement into the proximal direction decreases the liquid volume (also referred to as "active volume") within the metering cavity, while a piston movement in the distal direction increases the active volume. In operation, liquid is accordingly drawn into the metering cavity by a piston movement in the distal direction and expelled out of the metering cavity by a piston movement into the proximal direction. The terms "inwards" and "outwards" refer to radial directions perpendicular to the displacement axis. The inwards direction points from the periphery of the dosing cylinder towards the displacement axis. The outwards direction points from the displacement axis towards the periphery.

In some embodiments, the piston is a two-element piston with a hard piston element and a soft piston element. In such embodiments, the soft piston element acts as sealing member, with a circumferential surface of the soft piston member contacting the inner circumferential surface of the metering cavity, thus establishing a sealing and sliding engagement in the operational configuration.

In some embodiments with a two-element piston, the piston is injection-molded and the soft piston element is made from thermoplastic elastomers. This type of embodiment where the piston is made by two-component injection molding is particularly favorable regarding large scale manufacturing costs. For thermoplastic elastomers, however, creeping is particularly critical. Therefore, this disclosure is particularly favorable in this context. Alternatively, however, the piston may be generally made from a hard material, e.g., hard plastics, and a soft piston element is provided as dedicated separate component, e.g., as miniaturized elastomeric O-ring seal and mounted to the hard piston element only during assembly.

In some embodiments, the configuration switch member is movable from the storing position into the operational position by displacing the configuration switch member relative to the piston along the displacement axis. Via this relative displacement, the piston is radially extended, thus biasing the circumferential sealing member against the circumferential inner surface of the metering cavity and establishing the sealing.

Alternatively or additionally, the configuration switch member may, fully or in part, be radially movable with respect to the displacement axis for switching from the storing configuration to the operational configuration.

In some embodiments, the configuration switch member is arranged, at least partly, within a bore or recess of the piston. For such embodiments, movement of the configuration switch member from the storing position to the operational position is associated with a displacement of the configuration switch member within the bore or recess. Favorably, the configuration switch member is arranged in a bore or recess in a proximal section of the piston. The arrangement of the configuration switch member in a bore or recess of the piston allows a particularly compact design of the dosing unit.

In some embodiments, the configuration switch member overlaps, in the axial direction, with the circumferential sealing member. It is generally favorable to axially align the force that is exerted by the configuration switch member onto the circumferential sealing member in the operational configuration with the circumferential sealing member.

In some embodiments, the configuration switch member includes a spring member, the spring member being biased in the storing position and being fully or partly relieved upon movement from its storing position into its operational position For such embodiments, the movement of the spring member from its initial biased (i.e., deflected) configuration towards its released (i.e., non-deflected) configuration results in the circumferential sealing member being biased against the circumferential inner wall of the dosing cylinder. The corresponding biasing force is accordingly a spring force. As will be discussed in more detail below in the context of exemplary embodiments, the spring member may especially be realised by spring-loaded arms that extend parallel to the displacement axis.

In some embodiments, the piston and the configuration switch member are designed to force-lock and/or positively lock the configuration switch member relative to the piston in the operational position. Force locking may especially be realized via a radial force acting between the circumferential inner surface of the metering cavity, the piston, the piston, and the configuration switch member. Here, the soft piston element serves as resilient biasing member and is arranged between the metering cavity wall and the configuration switch member. The configuration switch member is favorably made from a hard material, such as hard plastics. For positive locking of the configuration switch member relative to the piston, interacting hooks, catches, protrusion, recesses and the like may be provided.

In some embodiments, the configuration switch member includes a stop member, the stop member being axially spaced apart from the piston in the storing position. Movement of the configuration switch member from the storing position into the operational position is associated with a movement of the stop member towards the piston. The stop member may especially be an, e.g., disk-shaped radial protrusion that is arranged proximal of the piston front surface in the storing position. The stop member hitting the piston surfaces stops the movement of the configuration switch member in the operational position.

In some embodiments with a stop member, the configuration switch member is arranged to be displaced from the storing position into the operational position via the stop member interacting with a blocking surface of the dosing cylinder.

In some embodiments, the piston includes or is operatively mechanically coupled to a threaded piston member, the threaded piston member being arranged to engage a threaded counter-member for displacing the piston. The threaded piston member may, e.g., include an outer thread that engages a threaded counter-member in form of an inner thread of a rotational drive sleeve. The drive sleeve may be part of the dosing unit or of a separate drive unit. Alternatively, an inner thread as threaded counter member may be provided as part of the dosing cylinder.

According to a further aspect, this disclosure provides an ambulatory infusion system. Typically, such ambulatory infusion system is designed to be continuously carried by a user over an extended time period and concealed from view. The ambulatory infusion system includes a dosing unit as described before as well as further below in the context of exemplary embodiments. The ambulatory infusion system further includes an electric drive unit, the drive unit operatively mechanically coupling to the piston for displacing the piston inside the metering cavity. In embodiments where the dosing unit includes a valve unit as discussed before, the drive unit may further couple to the valve unit for switching the valve unit between the filling configuration and the draining configuration.

According to a still further aspect, this disclosure provides a method for initializing a dosing unit of an ambulatory infusion system. The dosing unit of such ambulatory infusion system includes a dosing cylinder and a piston. The piston is arranged sliding displaceable along a displacement axis inside the dosing cylinder.

The method includes the steps of:
a) providing the dosing unit with a piston of the dosing unit being in a storing configuration, wherein a circumferential sealing member of the piston is mechanically relieved in the storing configuration;

b) moving a configuration switch member relative to the piston from a storing position into an operational position.

By moving the configuration switch member, the piston is switched from the storing configuration into an operational configuration. A sealing engagement of the circumferential sealing member and a circumferential inner surface of the metering cavity is thereby established.

In some embodiments, the step of moving the configuration switch member relative to the piston from the storing position into the operational position includes moving the piston in a proximal direction with a movement of the configuration switch member in the proximal direction being blocked by an interaction of the configuration switch member and the dosing cylinder.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

In the figures, the proximal direction is indicated by "p" while the distal direction is indicated by "d." Identical or substantially identical elements in various figures are generally referenced only once.

Figure 1:
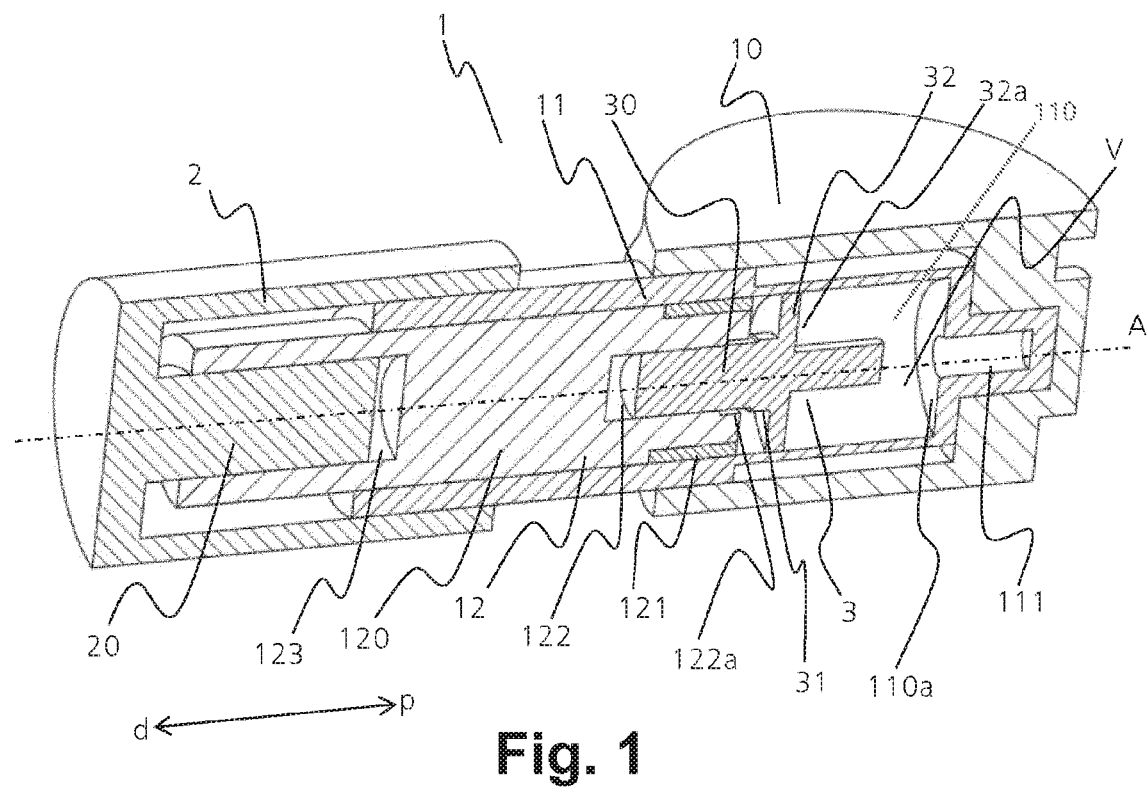
FIG. 1 shows an exemplary dosing unit in accordance with the present disclosure with the piston being in the storing configuration.

In the following, reference is first made to FIG. 1. FIG. 1 shows an exemplary embodiment of a dosing unit 1 in accordance with the present disclosure together with a drive sleeve 2 of an electric drive unit.

The dosing unit 1 includes a stationary part 10, a dosing cylinder 11, and a piston 12. Additionally, the dosing unit 1 includes a configuration switch or switch member 3.

The dosing cylinder 11 is rotatable and sealingly supported in a recess or dosing cylinder bore (not referenced) of the stationary part 10. The dosing cylinder 11 has a longitudinal symmetry axis which defines the displacement axis A.

The piston 12 has a body 120 that generally extends along the displacement axis A. Like the stationary part 10 and the dosing cylinder 11, the piston body 120 is made of hard plastics. In a proximal section of the piston 12, a circumferential sealing member 121 is arranged. The circumferential sealing member 121 is made from a comparatively soft material, in particular a thermoplastic elastomer (TPE), and is formed with the piston body 120 in an integral way by two-component injection molding. In combination, the body 120 and the sealing member 121 have a plane proximal front surface.

The dosing cylinder 11 is generally hollow and of tubular shape with an open distal and a closed proximal front surface. The inner volume of the dosing cylinder 11 forms a metering cavity of circular cross section. The metering cavity accordingly forms an elongated bore or recess of the dosing cylinder 11. The metering cavity has a metering cavity main section 110 and a proximal metering cavity recess 111. As compared to the metering cavity main section 110, the proximal metering cavity recess 111 is substantially shorter and has a substantially smaller inner diameter. The metering cavity main section 110 and the proximal metering cavity recess 111 are concentric with and extend along the displacement axis A. In operation, a variable volume V of the metering cavity 110, 111, proximal of the piston 12 and the configuration switch member 3, is filled with liquid (also referred to as "active volume"). Alternatively, the metering cavity may not be two-parted but have a cylindrical shape of a single diameter.

Distal from the piston body 120, the piston 12 has a threaded piston member 123 that is realized as innerthreaded tubular recess. The inner thread (not shown) of the threaded piston member 123 is, in an operational state, in engagement with a threaded counter-member 20 that is realized as outer-threaded pin of the drive sleeve 2 (outer thread not shown). The piston 12 and the dosing cylinder 11 are further in engagement via an anti-rotation member as known in the art (not shown). By rotating the drive sleeve 2, the piston 12 is accordingly linearly displaceable along the axis A within the dosing cylinder 11, in proximal or distal direction, respectively, thereby decreasing or increasing respectively the active volume V.

By a coupling mechanism (not shown), the dosing cylinder 11 is further selectively operatively and mechanically coupleable with the drive sleeve 2. When rotating the drive sleeve 2 in the coupled or engaged state, both the dosing cylinder 11 and the piston 12 are accordingly rotated in combination relative to the stationary part 10, substantially or fully without relative movement between the dosing cylinder 10 and the piston 11. When rotating the drive sleeve 2 in the uncoupled or disengaged state, only the piston 12 is axially displaced as explained before, while the dosing cylinder 11 does not move.

In a circumferential wall (side wall) at the proximal end of the proximal metering cavity recess 111, a dosing cylinder aperture (not visible) is arranged. An inlet aperture and an outlet aperture (both not visible) are further arranged in the stationary part 10. In dependence of the rotational position of the cylinder relative to the stationary part 10, the dosing cylinder aperture may fluidic couple the active volume V with the inlet aperture, or, alternatively, with the outlet aperture. Favorably, stops, blocks or the like are present that limit the movement of the dosing cylinder 11 relative to the stationary part 10.

In the following, operation of the configuration switch member 3 and associated features is explained in more detail. A distal section (not separately referenced) of the configuration switch member 3 is received in a configuration switch member recess 122 in a proximal area of the piston 12. The configuration switch member 3 has a cylindrical or pin-shaped configuration switch member body 30 and a disk-shaped stop or stop member 32, with the disk diameter corresponding to and being favorably slightly smaller than the outer diameter of the piston 12 and the inner diameter of the distal metering cavity 110, respectively. The configuration switch member 3 is typically made from hard plastics.

The diameters of the configuration switch member recess 122 and the configuration switch member body 30 are favorably adjusted such that the configuration switch member 3 is displaceable with respect to the piston 12 along the displacement axis A under substantial friction between the configuration switch member recess 122 and the configuration switch member body 30. Adjacent to and distal from the stop member 32, the configuration switch member 3 has a bracing member 31 that is exemplarily realized as ring-shaped protrusion (i.e., section of larger diameter). A corresponding piston bracing recess 122a is present in a proximal section of the piston body 120. The piston bracing recess 122a is realized as recess of a diameter slightly smaller than the bracing member 31.

FIG. 1 shows the dosing unit 1 in an initial state prior to its first use, with the active volume V not being filled with liquid and the configuration switch member 3 being in its storing position. The piston 12 is accordingly in its storing configuration. The dosing cylinder 11 and the piston 12, in particular the piston body 120 and the circumferential sealing member 121, are dimensioned such that the contact of the circumferential outer surface of the circumferential sealing member 121 on the one hand and the circumferential inner wall of the dosing cylinder 11, on the other hand, is loose. No or little mechanical stress is accordingly exerted onto the circumferential sealing member. In this state, no or only little sealing is present between the circumferential sealing member 121 and the dosing cylinder 11.

Figure 2:
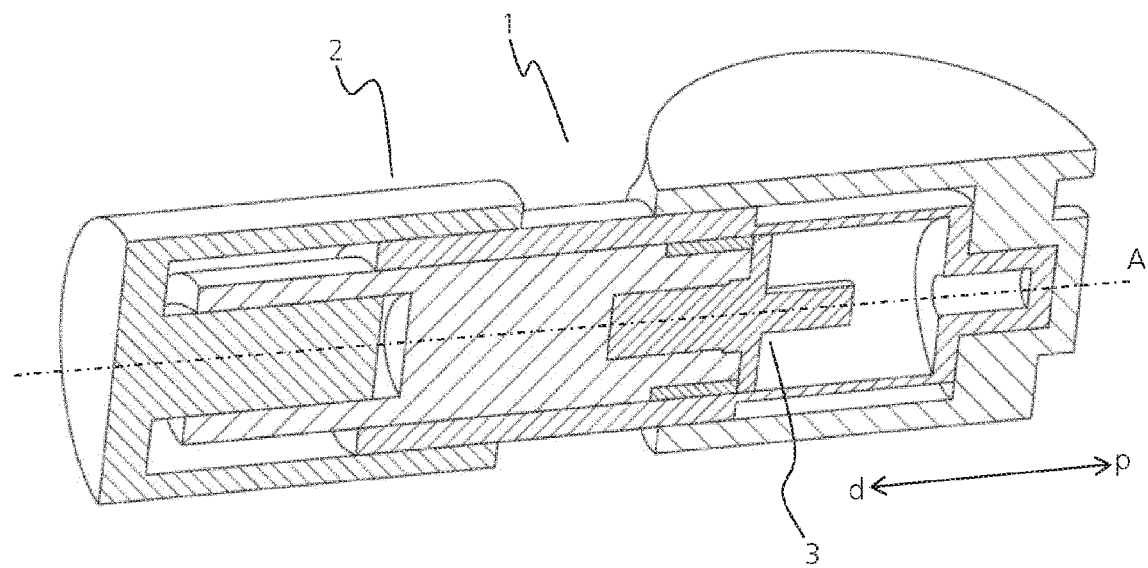
FIG. 2 shows the dosing unit of FIG. 1 with the piston being in the operational configuration.

In the following, reference is additionally made to FIG. 2. FIG. 2 shows the dosing unit 1 in its operational configuration. For switching the piston 12 from the storing configuration as shown in FIG. 1 into the operational configuration as shown in FIG. 2, the piston 12 is, together with the configuration switch member 3, displaced along the displacement axis A in proximal direction. During this process, the proximal pin-shaped section of the configuration switch member body 30 is introduced into the proximal metering cavity recess 111. Since the displacement of the plunger 12 and the configuration switch member 3 results in a decrease of the active volume V, the dosing cylinder aperture is favorably fluidic coupled with the outlet aperture, thus allowing initially present gas (typically air or an inert gas) to exit the dosing cylinder 11. Upon the stop member front surface 32a contacting or hitting the metering cavity front wall 110a as blocking surface, the configuration switch member 3 is stopped and further displacement is prevented.

Further advancement of the piston 12 in proximal direction is accordingly associated with a displacement of the configuration switch member 3 in distal direction relative to the piston 12. The configuration switch member body 30 is accordingly further inserted into the configuration switch member recess 122, favorably under frictional force as explained above. Finally, the bracing member 31 is pressed into the piston bracing recess 122a. Since the piston bracing recess 122a has a somewhat smaller diameter than the bracing member 31 as explained before, a proximal section of the piston body 120 is radially braced outwards. Thereby, the circumferential sealing member 121 is pressed and biased against the circumferential inner wall of the dosing cylinder 11, thus establishing fluid-tight sealing. Favorably, the piston body 120 is, at least in a proximal section, radially elastic, thus supporting the radial outwards bracing of the piston body 120. At its distal end (pointing towards the piston body 120), the ring-shaped bracing member 31 is favorably chamfered (not shown) to support introduction into the piston bracing recess 122a.

Figure 3:
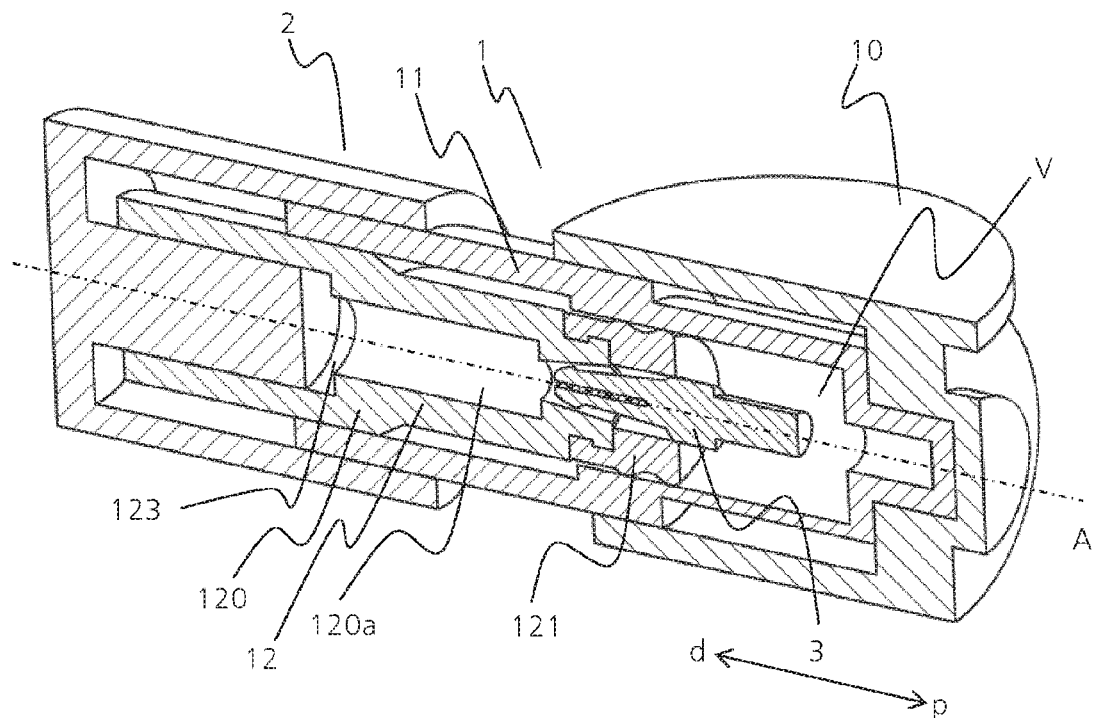
FIG. 3 shows a further exemplary dosing unit in accordance with the present disclosure with the piston being in the storing configuration.
Figure 4:
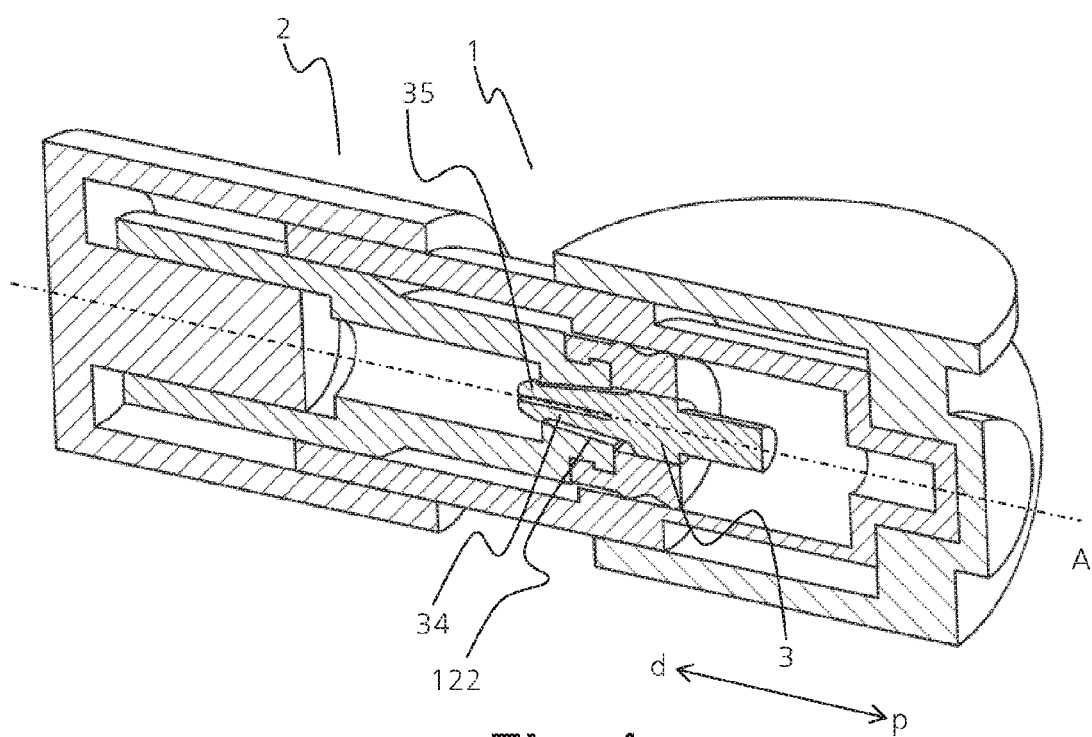
FIG. 4 shows the dosing unit of FIG. 3 with the piston being in the operational configuration.

In the following, reference is additionally made to FIG. 3 and FIG. 4, showing a further exemplary embodiment of a dosing unit 1 in accordance with the present disclosure. In FIG. 3, the piston 12 is in the storing configuration, while it is in the operational configuration in FIG. 4. In the following, only those elements and features are discussed that are different as compared to the previously discussed exemplary embodiment.

In the embodiment of FIG. 3 and FIG. 4, the piston 12 is a hollow tubular structure over its whole length. Proximal of the threaded piston recess 123, a proximal piston recess 120a of smaller diameter is arranged. Proximal to the proximal piston recess 120a, the configuration switch member recess 122 is arranged which has a frustro-conical shape in this embodiment.

The circumferential sealing member 121 is arranged proximal and flush with the piston body 120 and engages the piston body 120 via positive locking. The configuration switch member recess 122 extends through the circumferential sealing member 121 in form of an axial through-hole of the circumferential sealing member 121.

The configuration switch member 3 of this embodiment includes spring members in form of spring arms 34 and deflection protrusions 35 that are arranged at the distal ends of the spring arms 34 and point radially outwards. In the storing configuration as shown in FIG. 3, the spring arms 34 are radially deflected inwards from their unbiased configuration by the deflection protrusions 35 contacting the inner circumferential wall of the configuration switch member recess 122. The spring arms 34 are accordingly radially biased.

Similar to the before-discussed embodiment, switching from the storing configuration to the operational configuration is achieved by displacing the piston 12 in proximal direction while preventing displacement of the configuration switch member 3. At some point, the deflection protrusions 35 will exit the configuration switch member recess 122. The spring arms 34 will accordingly flex outward, towards their unbiased configuration as shown in FIG. 4. The spring arms 34 flexing outwards causes a corresponding radial outward flexing or bracing of the piston body 120 which is favorably radially elastic. Thereby, the circumferential sealing member 121 is pressed and biased against the circumferential inner wall of the dosing cylinder 11, thus establishing fluid-tight sealing.

The before-discussed exemplary dosing units in accordance with the present disclosure may be modified and/or varied in a number of ways.

While hard plastics are typically used for the components of the dosing unit 1 (with exception of the circumferential sealing member 121), other materials such as ceramics, glass, or metal may also be used for some or all of the components alone or in combination with other materials.

Furthermore, alternative drive arrangements may be used. In particular, rather than providing the threaded engagement between the drive sleeve 2 and the piston 12, a threaded engagement may be present between the piston 12 and the dosing cylinder 11. In such embodiments, an electric drive unit and the dosing unit 1 may be operatively mechanically coupled by a rotational engagement for torque transmission, while enabling free sliding movement of the piston 12 relative to the drive sleeve 2 in axial direction. In still further embodiments, no threaded engagement is present and the piston 12 operatively couples to a linear displaceable plunger rod of the electric drive system.

Furthermore, the valve switching for coupling the dosing cylinder aperture with the inlet aperture or outlet aperture may be realised in a different way. In particular, a functionally separate control valve may be provided for this purpose. In such embodiments, no rotation of the dosing cylinder 11 relative to the stationary member 10 is required. Furthermore, the stationary member 10 and the dosing cylinder 11 may be designed for axial rather than rotational sliding engagement. In such embodiments, valve switching is achieved by axially displacing the dosing cylinder 11 relative to the stationary member 10.

Further locking means may be provided at the piston body 120 and/or the configuration switch member 3 for locking the configuration switch member 3 relative to the piston 12 in the operational position by force locking and/or positive locking.

It is to be generally noted that the technical realization of all aspects of the dosing unit that are unrelated to the engagement and sealing between piston and dosing cylinder is not essential. Therefore, the dosing units of the before-described exemplary embodiments are exemplary. In particular, the EP 1970677, EP 2510962, EP 2510960, EP 2696915, EP 2457602, WO 2012/069308, WO 2013/029999, WO 2013/034159, EP 2163273, EP 2361646 each disclose dosing units and/or systems including a dosing unit that may be modified in accordance with the present disclosure. As discussed before in the general description, the dosing unit may especially comprise or be realized as drug cartridge of generally known design and as widely used in infusion systems and devices, e.g., infusion pumps, of the syringe-driver type.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

REFERENCE SIGNS

A displacement axis
V liquid-filled volume of metering cavity
d Distal
p Proximal
1 dosing unit
10 stationary part
11 dosing cylinder
110 distal metering cavity section
110a blocking surface/metering cavity front wall
111 proximal metering cavity recess
12 piston/plunger
120 piston body
120a proximal piston recess
120b locking protrusion counter shoulder
121 circumferential sealing member
122 configuration switch member recess
122a piston bracing recess
123 threaded piston member/threaded piston recess
2 drive sleeve
20 threaded counter-member
3 configuration switch member
30 configuration switch member body
31 bracing member
32 stop member
32a stop member front surface
34 spring arm/spring member
35 locking protrusion

What is claimed is:

1. A dosing unit for use in an ambulatory infusion system, the dosing unit comprising:
   a dosing cylinder having a circumferential inner surface;
   a piston displaceable within the dosing cylinder along a displacement axis, the piston having a circumferential sealing member;
   the piston having a storing configuration in which the circumferential sealing member is mechanically relieved and an operational configuration in which the circumferential sealing member is in sealing and sliding engagement with the circumferential inner surface; and
   a configuration switch member that is movable relative to the piston from a storing position to an operational position to switch the piston from the storing configuration to the operational configuration by biasing the circumferential sealing member radially outwardly into sealing engagement with the circumferential inner surface as the configuration switch member is moved into the operational position and wherein the configuration switch member is arranged at least partially within a bore or recess of the piston;
   wherein, when in the storing position, the configuration switch member includes a stop member axially spaced apart from the piston, wherein movement of the configuration switch member from the storing position into the operational position is associated with movement of the stop member towards the piston due to the stop member interacting with a blocking surface of the dosing cylinder and wherein the configuration of the stop member prevents entry of the stop member into the bore or recess of the piston.

2. Dosing unit according to claim 1, wherein the piston has a piston body made from a harder material than the material from which the circumferential sealing member is made.

3. Dosing unit according to claim 2, wherein the piston body is injection-molded and the circumferential sealing member is formed from a thermoplastic elastomer.

4. Dosing unit according to claim 1, wherein the movement of the configuration switch member relative to the piston comprises displacement relative to the piston along the displacement axis.

5. Dosing unit according to claim 1, wherein the configuration switch member is displaced further into the bore or recess of the piston as the configuration switch member moves from the storing position into the operational position.

6. Dosing unit according to claim 5, wherein the configuration switch member overlaps in an axial direction with the circumferential sealing member.

7. Dosing unit according to claim 1, wherein the configuration switch member includes a spring member that is fully or partly relieved upon movement of the configuration switch member from the storing position to the operational position.

8. Dosing unit according to claim 1, wherein the piston and the configuration switch member are configured to force-lock and/or positively lock the configuration switch member relative to the piston in the operational position.

9. A dosing unit for use in an ambulatory infusion system, the dosing unit comprising:
a dosing cylinder having a circumferential inner surface;
a piston displaceable within the dosing cylinder along a displacement axis, the piston having a circumferential sealing member;
the piston having a storing configuration in which the circumferential sealing member is mechanically relieved and an operational configuration in which the circumferential sealing member is in sealing and sliding engagement with the circumferential inner surface; and
a configuration switch member that is movable relative to the piston from a storing position to an operational position to switch the piston from the storing configuration to the operational configuration and wherein the configuration switch member is arranged at least partially within a bore or recess of the piston;
wherein, when in the storing position, the configuration switch member includes a stop member axially spaced apart from the piston, wherein movement of the configuration switch member from the storing position into the operational position is associated with movement of the stop member towards the piston due to the stop member interacting with a blocking surface of the dosing cylinder and wherein the configuration of the stop member prevents entry of the stop member into the bore or recess of the piston; and
wherein the dosing cylinder defines a metering cavity having a main section and a recess, the recess having a smaller inner diameter than the main section, and wherein the configuration switch member includes a pin shaped section projecting proximally of the radially outwardly projecting stop member, the pin shaped section being received in metering cavity recess.

10. Dosing unit according to claim 1, wherein the dosing unit further comprises a stationary part having an inlet aperture and an outlet aperture and the dosing unit is reversibly switchable between a filling configuration and a draining configuration by moving the dosing cylinder relative to the stationary part, and wherein the dosing cylinder is fluidly coupled with the inlet aperture in the filling configuration and the dosing cylinder is fluidly coupled with the outlet aperture in the draining configuration.

11. Dosing unit according to claim 1, wherein the piston includes or is operatively coupled to a threaded piston member, the threaded piston member configured to engage a threaded counter-member for displacing the piston.

12. Dosing unit according to claim 1, further comprising an electric drive unit operatively coupled to a drive sleeve of the dosing unit for displacing the piston inside the dosing cylinder.

13. A method for initializing a dosing unit of an ambulatory infusion system, the dosing unit including a dosing cylinder and a piston displaceable within the dosing cylinder along a displacement axis, the method comprising:
(a) providing the dosing unit with the piston initially in a storing configuration in which a circumferential sealing member of the piston is mechanically relieved; and
(b) moving a configuration switch member relative to the piston from a storing position into an operational position and thereby switching the piston from the storing configuration into an operational configuration to establish a sealing and sliding engagement of the circumferential sealing member and a circumferential inner surface of the dosing cylinder and moving the piston in a proximal direction relative to the cylinder with a movement of the configuration switch member in the proximal direction being blocked by an interaction of the configuration switch member and the dosing cylinder; and
(c) wherein the dosing cylinder defines a metering cavity having a main section and a recess, the recess having a smaller inner diameter than the main section, and wherein the configuration switch member includes a radially outwardly projecting stop member and a pin shaped section projecting proximally of the radially outwardly projecting stop member, and wherein the interaction of the configuration switch member and the dosing cylinder of step (b) includes the pin shaped section being received in metering cavity recess and the radially outwardly projecting stop member contacting a blocking surface of the dosing cylinder.

14. Method according claim 13, wherein the interaction of the configuration switch member and the dosing cylinder of step (b) includes moving the piston in a proximal direction with a movement of the configuration switch member in the proximal direction being blocked by engagement of the radially outwardly projecting stop member with the blocking surface.

15. A dosing unit for use in an ambulatory infusion system, the dosing unit comprising:
a dosing cylinder having a circumferential inner surface;
a piston displaceable within the dosing cylinder along a displacement axis, the piston having a circumferential sealing member;
the piston having a storing configuration in which the circumferential sealing member is mechanically relieved and an operational configuration in which the circumferential sealing member is in sealing and sliding engagement with the circumferential inner surface; and
a configuration switch member;
wherein movement of the piston relative to the dosing cylinder along the displacement axis causes the configuration switch member to move relative to the piston along the displacement axis to switch the piston from the storing configuration to the operational configuration and wherein the circumferential sealing member is biased radially outwardly into sealing engagement with the circumferential inner surface as the configuration switch member is moved relative to the piston to switch the piston into the operational configuration; and
wherein the configuration switch member includes a spring member that is at least partially relieved upon movement of the configuration switch member from the storing position to the operational position, the spring member being moved relative to the piston along the displacement axis with the configuration switch member as the piston is moved from the storing configuration to the operational configuration.

16. A dosing unit for use in an ambulatory infusion system, the dosing unit comprising:
a dosing cylinder having a circumferential inner surface;
a piston displaceable within the dosing cylinder along a displacement axis, the piston having a circumferential sealing member;
the piston having a storing configuration in which the circumferential sealing member is mechanically relieved and an operational configuration in which the circumferential sealing member is in sealing and sliding engagement with the circumferential inner surface; and a configuration switch member;

wherein movement of the piston relative to the dosing cylinder along the displacement axis causes the configuration switch member to move relative to the piston along the displacement axis to switch the piston from the storing configuration to the operational configuration;

wherein the configuration switch member includes a spring member that is at least partially relieved upon movement of the configuration switch member from the storing position to the operational position, the spring member being moved relative to the piston along the displacement axis with the configuration switch member as the piston is moved from the storing configuration to the operational configuration; and wherein the movement of the piston is in a proximal direction and the movement of the configuration switch member is in a distal direction opposite the proximal direction.

17. The dosing unit of claim 16, wherein the movement of the piston in the proximal direction causes the configuration switch member to contact the cylinder and thereby causes the movement of the configuration switch member relative to the piston.

18. The dosing unit of claim 17, wherein the piston comprises a recess into which a portion of the configuration switch member is inserted during the contact of the configuration switch member with the cylinder.

19. The dosing unit of claim 15, wherein the circumferential sealing member moves with the piston along the displacement axis during the movement of the piston.

20. The dosing unit of claim 15 wherein the spring member comprises a plurality of spring arms, each of the spring arms including a radially outwardly projecting protrusion.

21. The dosing unit of claim 20 wherein the piston defines a bore wherein a first portion of the bore has a larger diameter than a second portion of the bore, the second portion of the bore defining a frustoconical surface, and wherein, in the storing configuration, the protrusions on the spring arms are disposed within the second portion of the bore and movement of the piston into the operational configuration moves the protrusions from the second portion of the bore to the first portion of the bore, engagement of the protrusions by the frustoconical surface of the second portion biasing the spring arms radially inwardly.

* * * * *